(12) United States Patent
Singh et al.

(10) Patent No.: US 6,423,075 B1
(45) Date of Patent: Jul. 23, 2002

(54) UTERINE CANNULA AND PELVIC SUPPORT FOR GYNECOLOGICAL LAPAROSCOPY

(76) Inventors: Jiwan Steven Singh, 231 Timberlane Drive, Woodvale WA 6026 (AU); Stuart Hall, PO Box 292, Bentley WA 6982 (AU)

( * ) Notice: Subject to any disclaimer, the term of this patent is extended or adjusted under 35 U.S.C. 154(b) by 80 days.

(21) Appl. No.: 09/638,369

(22) Filed: Aug. 15, 2000

(30) Foreign Application Priority Data

May 22, 2000 (AU) .............................................. 36354/00

(51) Int. Cl.⁷ .............................................. A61B 1/303
(52) U.S. Cl. .............................. 606/119; 128/DIG. 26; 600/204
(58) Field of Search .......................... 606/119; 600/204, 600/562, 564, 570; 604/264, 275, 278, 279, 164.01, 174; 128/DIG. 6, DIG. 26

(56) References Cited

U.S. PATENT DOCUMENTS

| | | | | |
|---|---|---|---|---|
| 4,000,743 A | * | 1/1977 | Weaver ............... | 128/DIG. 26 |
| 5,368,598 A | * | 11/1994 | Hasson ................ | 128/898 |
| 5,603,689 A | * | 2/1997 | Lucini ................ | 600/201 |
| 5,797,899 A | * | 8/1998 | Tilton, Jr. ........... | 604/181 |
| 5,840,077 A | * | 11/1998 | Rowden et al. ........ | 606/119 |
| 6,174,317 B1 | * | 5/2001 | Engman ................ | 606/119 |
| 6,235,037 B1 | * | 5/2001 | East et al. ........... | 606/119 |
| 6,264,604 B1 | * | 7/2001 | Kieturakis et al. ..... | 600/201 |

* cited by examiner

Primary Examiner—William E. Tapolcai
(74) Attorney, Agent, or Firm—Allen, Dyer, Doppelt, Milbrath & Gilchrist, P.A.

(57) ABSTRACT

The instrument 10 for gynecological laparoscopy includes a cervical funnel 12 and an intra-uterine cannula 14 disposed axially within the funnel 12. Funnel 12 includes a hollow tube 16 having a proximal end 18 adapted to be inserted into the vagina of a patient. A hollow cone-shaped member 20 is provided at the proximal end 18. The cannula 14 has an outer sheath 58 provided at one end with a threaded cone 60 that threadingly engages the cervix to seal the uterus. An inner manipulation shaft 62 passes through the sheath 58 and cone 60 to allow manipulation of the uterus. The instrument 10 is supported by a support 92 that would be typically attached to an operating table or bed 96. Support 92 allows the position of the instrument 10 to be varied at will by the surgeon thus alleviating the need of the surgeon or a pelvic assistant to physically support the instrument 10. Seal 192 in the shape of a conical frustum is placed over the cone-shaped member 20 prior to insertion into the vagina. The seal 192 forms a seal about end 196 against the vaginal wall and about end 194 on the tube 16 to prevent loss of pneumoperitoneum during surgery.

22 Claims, 15 Drawing Sheets

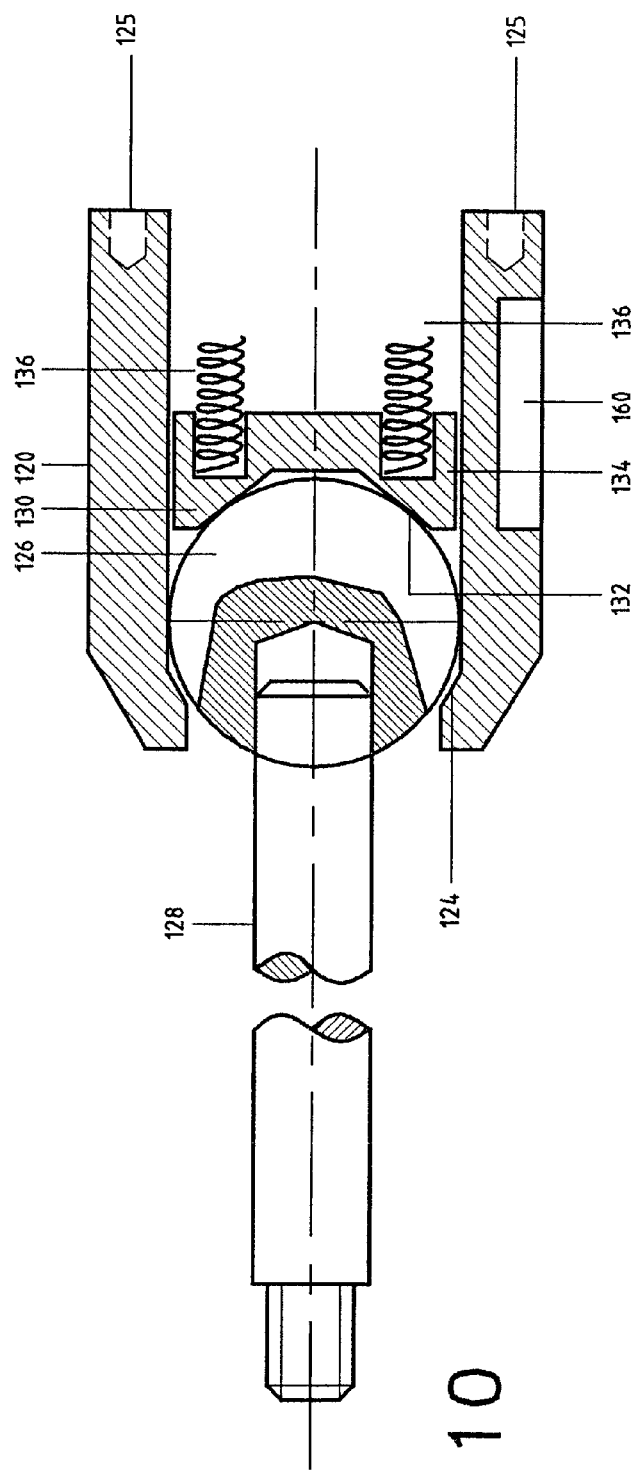
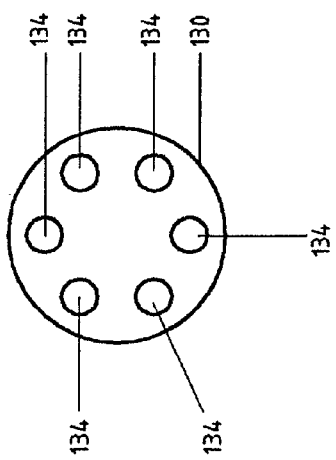
FIG. 10
FIG. 11

UTERINE CANNULA AND PELVIC SUPPORT FOR GYNECOLOGICAL LAPAROSCOPY

CROSS-REFERENCE TO RELATED APPLICATION

This application claims priority to and hereby incorporates by reference Australian Patent Application No. 36354/00, filed May 22, 2000.

FIELD OF THE INVENTION

The present invention relates to a uterine cannula and pelvic support for gynecological laparoscopy.

BACKGROUND

Gynecological laparoscopic surgery requires a pelvic assistant to hold and manipulate uterine cannulas at the command of the gynecologist.

Two types of known uterine cannulas are the Leech-Wilkinson intra-uterine cannula and the Spackman intra-uterine cannula. The Leech-Wilkinson cannula is in the form of an elongate hollow tube having a threaded cone provided about its distal end. The cannula is inserted through the vagina and the cone threading engaged with the cervix by rotation of the cannula to thereby seal the uterus. Fluid is then passed through the cannula to inflate the uterus and check for blockages. It is found that the cone seal formed at the end of the Leech-Wilkinson cannula forms a particularly effective seal preventing the leakage of fluid used during hydro tubation. However, a significant drawback with the Leech-Wilkinson cannula is that it does not allow intra-uterine manipulation during hydro tubation.

The Spackman cannula is in the form of a elongate hollow tube having a bulb formed at a distal end for forming a press seal with the cervix and a curved manipulator formed integrally with the bulb that extends into the uterus. The manipulator is provided with one or more outlet ports so that fluid can be delivered by the cannula into the uterus. The manipulator at the end of the Spackman cannula does allow for a small degree of intra-uterine manipulation. However in practice the seal formed by the bulb at the end of the cannula is often ineffective. As a result, substantial volume of the fluid may leak passed the cervix making the hydro tubation procedure inconclusive. To overcome this problem the Spackman cannula is provided with an adjustable plate for holding vulsellum forceps. The forceps are used to pinch the cervix into tight contact with the bulb to improve the seal. However it would be appreciated that when the vulsellum forceps are used, the manipulator can only be turned by a limited degree because the forceps would otherwise cause tearing of the cervix. Therefore in order to effectively use the manipulator on the Spackman cannula, the forceps must be released during manipulation thereby leading to a deterioration in the seal formed with the cervix. Further, the intra uterine tip of the Spackman cannula has a fixed length.

The use of the pelvic assistant during gynecological laparoscopy have several drawbacks. For long procedures, for example sometimes up to 20 minutes in a set position, the assistant becomes physically fatigued and is unable to maintain the desired orientation of the cannula. A further disadvantage is that because the assistant relies on oral instructions from the doctor the correct positioning of the cannula is an iterative process and therefore the time taken to correctly position the cannula is significantly greater than would be the case if the doctor could adjust the position. Further, the use of an assistant increases costs of the procedure as the assistant becomes a dedicated member of the surgical team.

More recently there has been a trend towards total laparoscopic hysterectomy and laparoscopic pelvic floor repair. Various devices have been incorporated to help facilitate this procedure, from uterine manipulators to vaginal tubes. The use of the vaginal tubes has been to provide cervical-vaginal delineation. Some of the uterine manipulators, although efficient, are difficult to use, have various parts that are easily misplaced and are, in general, bulky instruments. Moreover, almost all of them require a pelvic assistant, usually a doctor or a nurse, to hold the manipulator in place during the operation or to move it on command by the laparoscopic surgeon.

In the current art form, during total laparoscopic vaginal delivery, the vaginal vault is divided from the cervix to enable delivery of the uterus through the vagina. Various vaginal tubes have been used to delineate tissue plane and facilitate this procedure. The vaginal tubes may be made from various materials. A metal tube is used by surgeons who use CO2 lasers to cut the vaginal vault, while a plastic tube is used by those who use electrocautery, as it does not conduct electricity.

In the current art form, the surgeon requires a pelvic assistant, usually a nurse or a doctor, during laparoscopic surgery. Fatigue and musculo-skeletal problems are some of the costs to the pelvic assistant. For the hospital, it is costly to assign staff to carry out mechanical and time consuming tasks. The assistant will be required from time to time, at the direction of the surgeon, to change the position of the manipulator or vaginal tube. Firm pressure is required to keep the vaginal vault taut and while it is being divided from the cervix. Failure to maintain pressure on the vaginal vault, via the tube, may result in excessive bleeding. The vaginal wall is stretched, resulting in the blood vessels in the vaginal tissue being compressed by the pressure of the tube against the vaginal vault, thus resulting in the blood vessels being sealed during incision of the vaginal vault. The bladder may also be in danger of being damaged if pressure is lost during excision, as the edge of the vaginal tube keeps the bladder away from the vaginal wall as it is being incised. Uncontrolled or sudden loss of pressure and the tube against the vagina may result in excessive bleeding or bladder damage.

After the cervix has been detached from the vaginal vault, the uterus is delivered through the vaginal vault. Loss of pneumoperitoneum occurs and insertion of a vaginal tube with a sealed end is required to restore the pneumoperitoneum. A suture is usually placed in the hollow of the tube before it is inserted into the vagina. The needle of the suture is picked up with a laparoscopic needle holder and the vaginal vault sutured laparoscopically. The needle is then pushed through the vault into the vaginal tube for extraction as the vaginal tube is withdrawn from the vagina. A knot is made in the suture and secured through the vagina.

From time to time during the procedure an assistant is required to rotate the vaginal tube and hold it in position as requested by the surgeon.

Laparoscopic pelvic floor repair requires a vaginal probe and a rectal probe to delineate both structures to the laparoscopic surgeon. A pelvic assistant is therefore required to hold both probes. The availability of a pelvic assistant has been previously mentioned above.

SUMMARY

It is an object of the present invention to provide a medical instrument that facilitates a high degree of control and manipulation of the uterus during gynecological surgery.

According to the present invention there is provided a medical instrument for gynecological surgery comprising at least:

a cervical funnel having an elongated hollow tube with a proximal end for insertion into the vagina of a patient and a hollow substantially cone-shaped member provided at the proximal end of the hollow tube, the cone-shaped member having an outer diameter that reduces in a direction extending toward a distal end of the hollow tube and having a mouth with an inner diameter greater than the diameter of the opening of the patient's cervix; and, an intra-uterine cannula having: an outer sheath axially and rotatably moveable within said hollow tube, the outer sheath having a proximal end and an opposite distal end respectively locatable outside the proximal and distal ends of the hollow tube; sealing means provided at the proximal end of the sheath for engaging the cervix to seal the patient's uterus; and, an inner manipulation shaft axially and rotatably moveable within the outer sheath and extending axially through the sealing means.

Preferably the mouth of said cone-shaped member is formed with a protruding lip that extends along a portion of the circumference of the mouth for lifting a section of the vaginal vault away from adjacent internal organs.

Preferably the lip extends about the circumference of the mouth through an arc that subtends an angle of about 120°.

Preferably the lip protrudes at an angle of about 45° to the longitudinal axis of the cone-shaped member, for a distance of about 5 mm to 10 mm.

Advantageously, a mark is provided at the distal end of the hollow tube corresponding to the angular position of a midpoint of said lip so that a surgeon can visualize the position of the lip during a surgical procedure.

Preferably said cone-shaped member is made from a plastics material.

Preferably the cone-shaped member has a maximum outside diameter of between 30 mm to 50 mm, and more typically between 40 mm to 45 mm.

Preferably said cone-shaped member is removably attached to the proximal end of the hollow tube to facilitate replacement if damaged during a surgical procedure.

Preferably said hollow tube is made from an autoclavable material including stainless steel and has an outside diameter of between 10 mm to 30 mm, and more typically between 15 mm to 20 mm.

Preferably said sealing means is in the form of a cone having a thread formed along its outer surface with a large diameter end of the cone disposed adjacent the proximal end of said outer sheath.

Preferably said medical instrument further includes releasable locking means for releasably locking said inner manipulation shaft to said outer sheath.

Preferably said medical instrument further includes a support for supporting said intra-uterine cannula and cervical funnel, said support including an arm for coupling to a patient support to allow adjustment of the position of the support in a direction of the length of the arm; an adjustable joint attached to the arm providing at least one further degree of motion; an extendible member coupled to the joint; and, an instrument holder attached to an end of the extendible member for holding said intra-uterine cannula.

Preferably said joint provides three degrees of rotational motion to allow pitch, roll and yaw position control of the extendible member and thus the cannula.

Preferably the joint is a ball joint provided with releasable locking means which, when in the locked state, locks the position of the extendible member and when in the unlocked state allows adjustment of the position of the extendible member.

Preferably the extendible member is telescopically extendible.

Preferably said support further includes a clamp for releasably coupling the extendible member to the joint to allow adjustment of the position of the extendible member in a direction of its length.

BRIEF DESCRIPTION OF THE DRAWINGS

An embodiment of the present invention will now be described by way of example only with reference to the accompanying drawings in which:

FIG. 10 is a sectional view of a ball joint incorporated in the support depicted in FIG. 9A and 9B;

FIG. 11 is a top view of a friction pad incorporated in the ball joint;

DETAILED DESCRIPTION OF THE PREFERRED EMBODIMENTS

Figure 1:
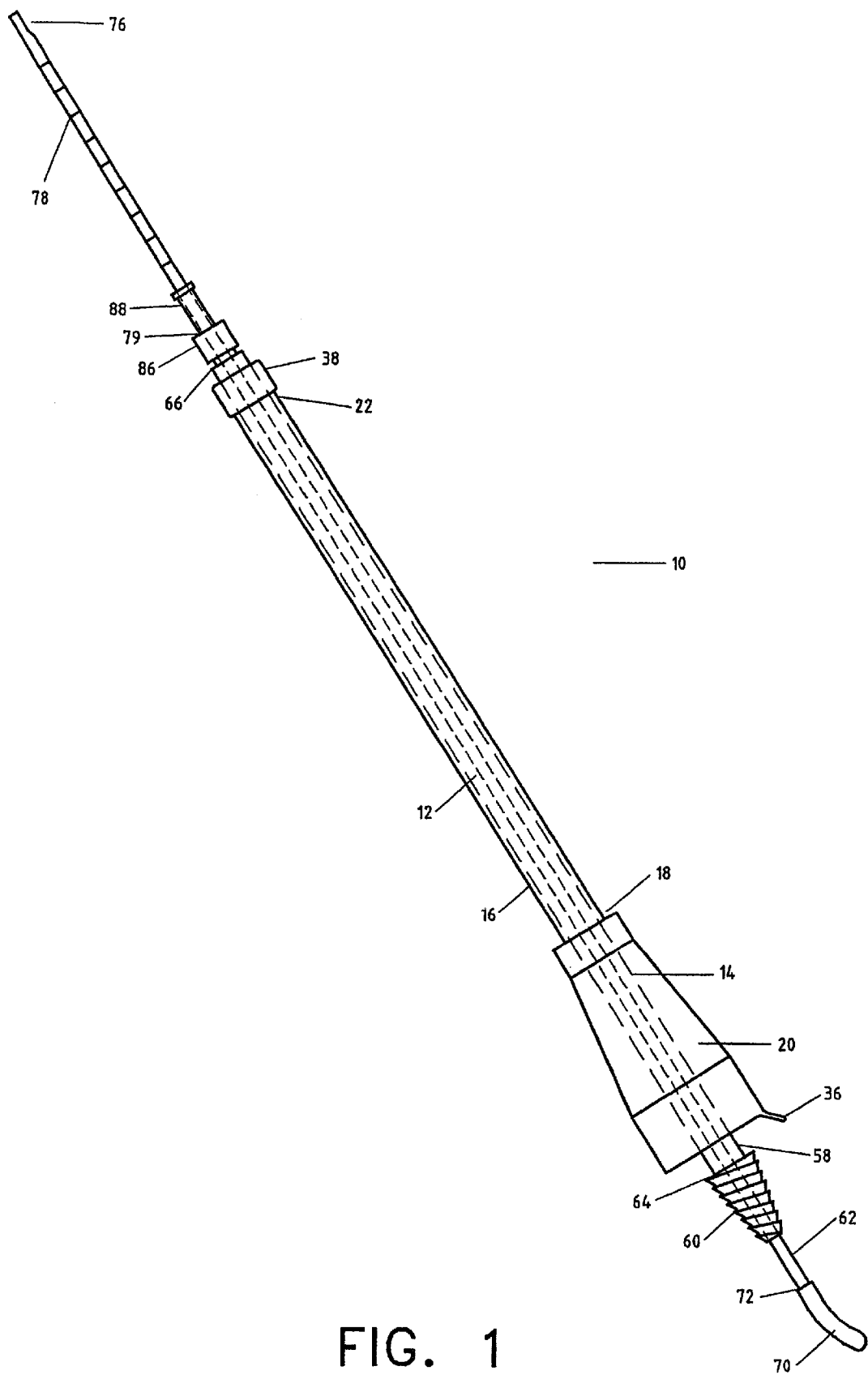
FIG. 1 is a schematic representation of the medical instrument.
Figure 3:
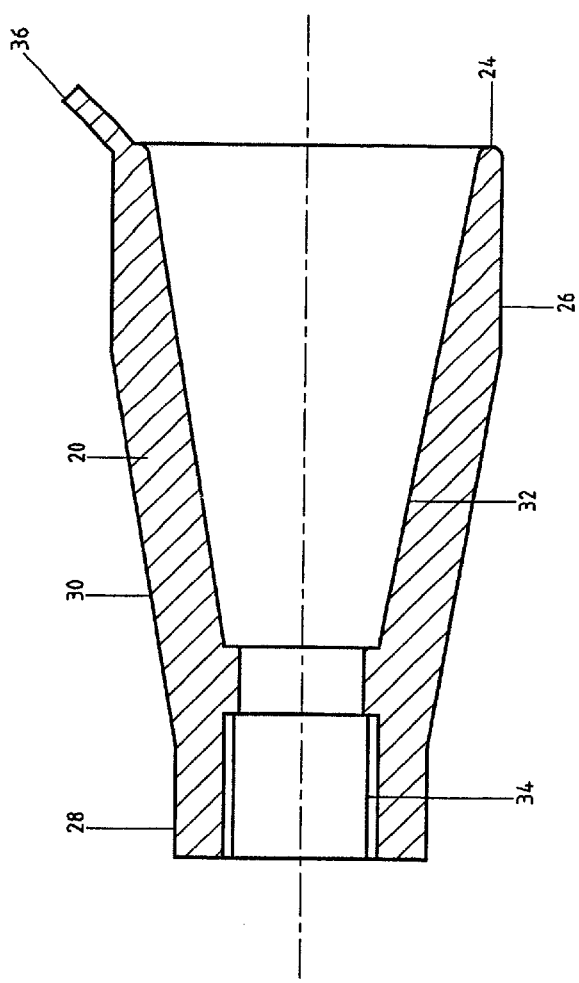
FIG. 3 is a cross-sectional view along the line A—A shown in FIG. 2 through the cone-shaped member of the funnel.

FIG. 1 depicts a preferred embodiment of the medical instrument 10 for use in gynecological surgery and in particular laparoscopic hysterectomy. The instrument 10 comprises a cervical funnel 12 and a SINGH intra-uterine cannula 14 disposed axially within the funnel 12. The funnel 12 comprises an elongate hollow tube 16 having a proximal end 18 adapted to be inserted into the vagina of a patient (not shown). A hollow substantially cone-shaped member 20 is provided at the proximal end 18 of the hollow tube 16. The cone-shaped member 20 has an outer diameter that reduces in a direction extending toward a distal end 22 of the hollow tube 16. The cone-shaped member 20 has a mouth 24, as can be seen most clearly in FIG. 3, having an inner diameter greater than the opening of the patient's cervix.

During total laparoscopic hysterectomy the vaginal vault is divided from the cervix to enable delivery of the uterus through the vagina. The cone-shaped member 20 of the cervical funnel 12 helps to delineate this tissue plane during surgery. For this purpose, the mouth 24 is seated about the opening of the cervix and firm pressure is applied to keep the vaginal vault taut whilst it is being divided from the cervix. When using a conventional vaginal tube, an assistant must hold the vaginal tube firmly during the procedure, as the muscle tone of the vaginal walls tended to expel the tube from the vagina. By contrast, because the cervical funnel 12 is provided with the cone-shaped member 20 of reducing outer diameter toward the relatively narrow hollow tube 16, it does not tend to be expelled by the vaginal wall muscle tone. Hence the cervical funnel does not require constant pressure to actively hold it in place during incision of the vaginal vault at hysterectomy.

Furthermore, pressure from the mouth 24 of the cone-shaped member 20 against the vaginal vault causes stretching of the blood vessels in the vaginal tissue, and the resulting compression by the pressure of the funnel 12 against the vaginal vault results in the blood vessels being sealed during incision of the vaginal vault with electrocautery.

The cone-shaped member 20 is preferably made from a suitable plastics material. For example, an acetal resin, such as DELRIN, is preferred. Being of plastics material, it allows electrocautery of the vaginal vault with electric current. The maximum outer diameter of the member 20 is typically between approximately 30 mm to 50 mm, and more typically between 40 mm to 45 mm. As can be seen most clearly in FIG. 3, in this embodiment the outer surface of the cone-shaped member 20 is formed with a first cylindrical surface 26 defining a maximum outer diameter of the member 20, and a second cylindrical surface 28 defining a minimum outer diameter of the cone-shaped member 20. The first and second surfaces 26, 28 are connected by an intermediate conical surface 30. The conical surface 30 has an incline of approximate 10° with respect to the first and second cylindrical surfaces 26, 28. The bulk of the hollow interior of the cone-shaped member 20 is defined by a second conical surface 32 inclined at an angle of 7.5° relative to the first and second cylindrical surfaces 26, 28, which are parallel to the longitudinal axis of the cone-shaped member 20.

The cone-shaped member 20 is preferably removably attached to the proximal end 18 of the tube 16. In this embodiment this is achieved by providing thread 34 on the inside of the second cylindrical surface 28 for screw-threaded attachment to the proximal end 18 of the tube 16. However, any suitable form of attachment may be employed, for example, a click-on connection or a bayonet-type connection.

Figure 2:
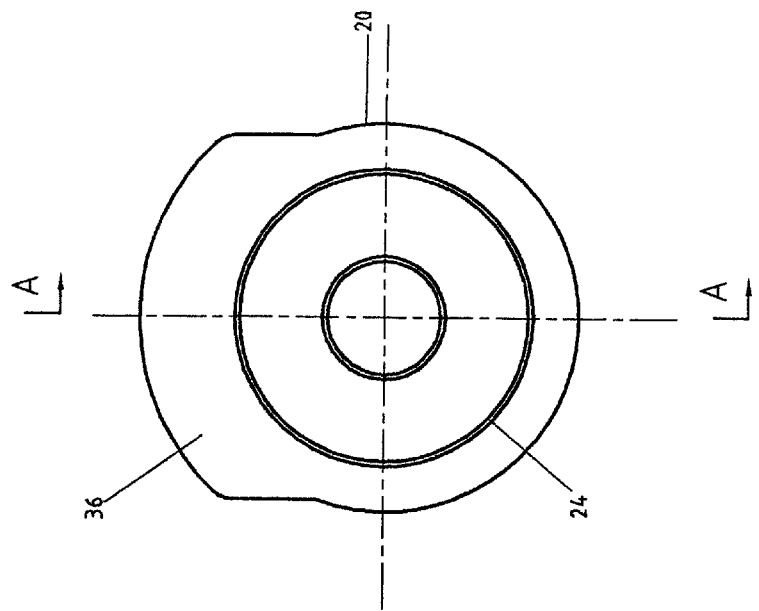
FIG. 2 is an end view of the surgical funnel incorporated in the instrument shown in FIG. 1, viewed from the proximal end of the funnel.

The mouth 24 is formed with a protruding lip 36 that extends along a portion of the circumference of the mouth as shown most clearly in FIG. 2. The lip 36 forms a cutting edge in the sense that tissue is cut, using another cutting instrument, against the lip 36. That is lip/cutting edge 36 forms a backing or support for tissue while it is being cut. The cutting edge is not in itself an edge that makes a cut. In this embodiment the lip 36 protrudes at an angle of approximately 45° to the longitudinal axis of the funnel, for a distance of between 5 mm to 10 mm. Typically the lip extends about the circumference of the mouth 24 through an arc that subtends an angle of approximately 120°. A mark is provided at the distal end of the hollow tube 16 to indicate the angular position of a midpoint of the lip 36, so that the surgeon can ascertain the position of the lip 36 during a surgical procedure.

During a surgical procedure the lip 36 can be positioned to lift a section of the vaginal wall away from adjacent internal organs, such as the bladder and the bowels. The bladder and rectum may be in danger of being damaged during laparoscopic hysterectomy. The lip 36 of the cervical funnel 12 keeps the bladder away from the vaginal wall as it is being incised. Rotation of the funnel 12 allows an appreciation of where the vaginal wall is in relation to the bladder. Further as the lip 36 rotates it stretches the vaginal wall.

The hollow tube 16 is preferably made from autoclavable material such as stainless steel and has an outside diameter of between 10 mm to 30 mm. In the illustrated embodiment the tube 16 has an outer diameter of 16 mm and is approximately 150 mm in length.

Figure 5:
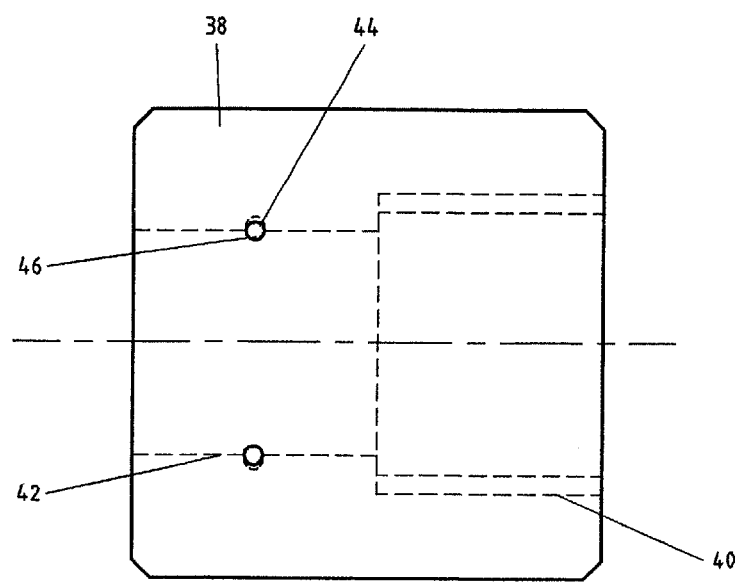
FIG. 5 is a side view of a cap for the funnel.

The funnel 12 also includes a cap 38 provided at its distal end 22. An enlarged side view of the cap 38 is shown in FIG. 5. The cap 38 is provided with an internal thread 40 to allow screw-threaded attachment to the distal end 22 of the tube 16. An aperture 42 is provided axially through the cap 38 to provide access for the cannula 14 and other surgical instruments that may be employed during the operation. The aperture 42 is provided with a circumferential groove 44 for seating an O-ring 46 which assists in forming a seal with the outer surface of the cannula 14.

Figure 4:
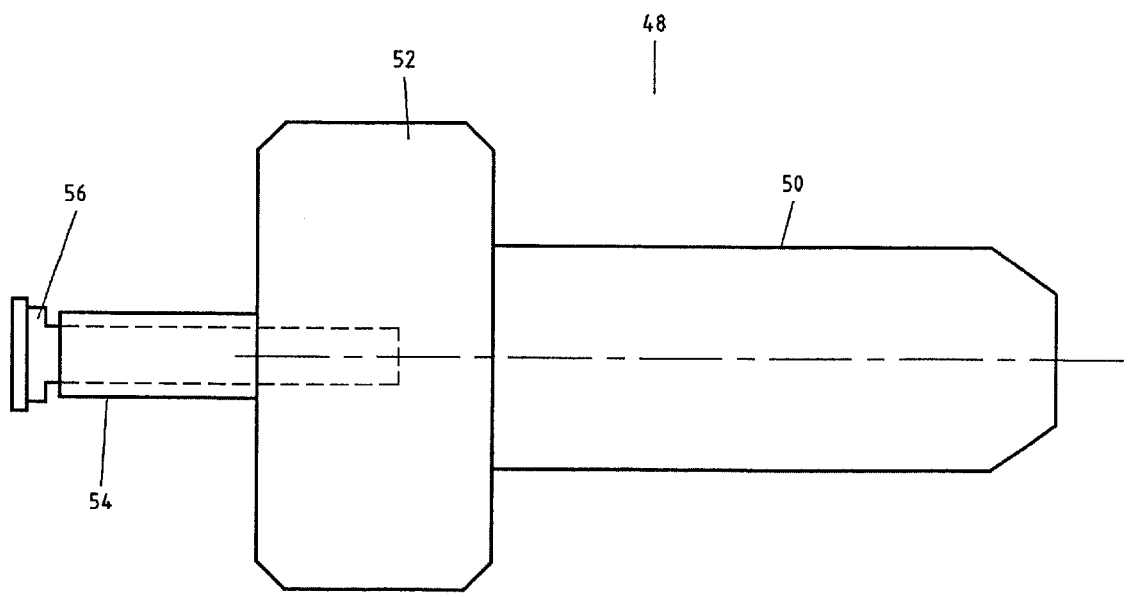
FIG. 4 is a side view of a plug that can be incorporated in the surgical funnel.

A plug 48 (shown in FIG. 4) is also provided to fill the aperture 42 to maintain pneumoperitoneum during the final suturing of the vagina vault at the end of the laparoscopic hysterectomy procedure. The plug 48 is provided with a cylindrical stub 50 that fits inside the aperture 42 and an increased diameter head 52 that abuts against the free end of the cap 38. The O-ring 46 maintains a seal about the stub 50 to maintain pneumoperitoneum. An axially rotatable cylindrical sleeve 54 is fastened on the outside of the head 52 by a screw 56. In use, the sleeve 54 can be gripped by the instrument support (described below) allowing the plug 48 and the cervical funnel 12 to rotate about its longitudinal axis.

Referring to FIG. 1, the SINGH intra-uterine cannula 14 comprises an outer sheath 58, sealing means in the form of a threaded cone 60 and an inner manipulation shaft 62. The outer sheath 58 is in the form of an elongate metal tube. The tube has a proximal end 64 and an opposite distal end 66. When disposed within the funnel 12, the proximal end 64 extends beyond or; the proximal end 18 of the tube 16 and the distal end 66 of the shaft 58 extends beyond the distal end 22 of the tube 16.

Figure 6:
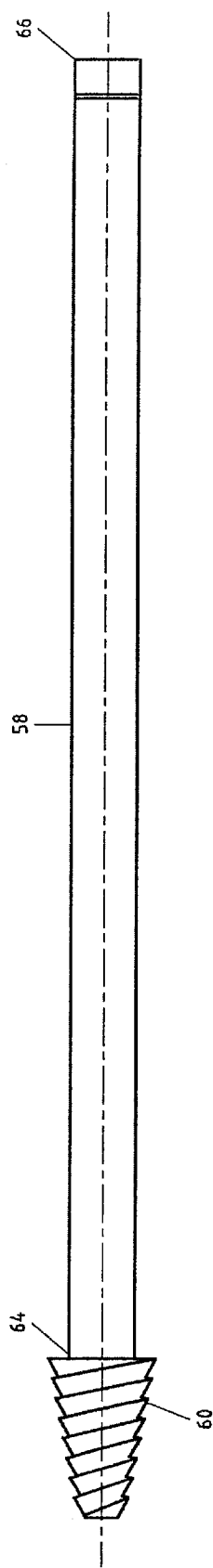
FIG. 6 is a side view of the outer shaft of the intra-uterine cannula incorporated in the instrument shown in FIG. 1.

As is apparent from FIGS. 1 and 6, the cone 60 is formed with its largest diameter end adjacent and attached to the proximal end 64 of the outer sheath 58. The cone 60 reduces in diameter in a direction away from the distal end 66. An internal axial bore is formed through the cone 60 through which the shaft 62 extends.

When in use, the SINGH intra-uterine cannula 14 is inserted through the vagina and the sheath 58 is rotated about its longitudinal axis so that the cone 60 threadingly engages the cervix so as to seal the uterus.

Figure 7:
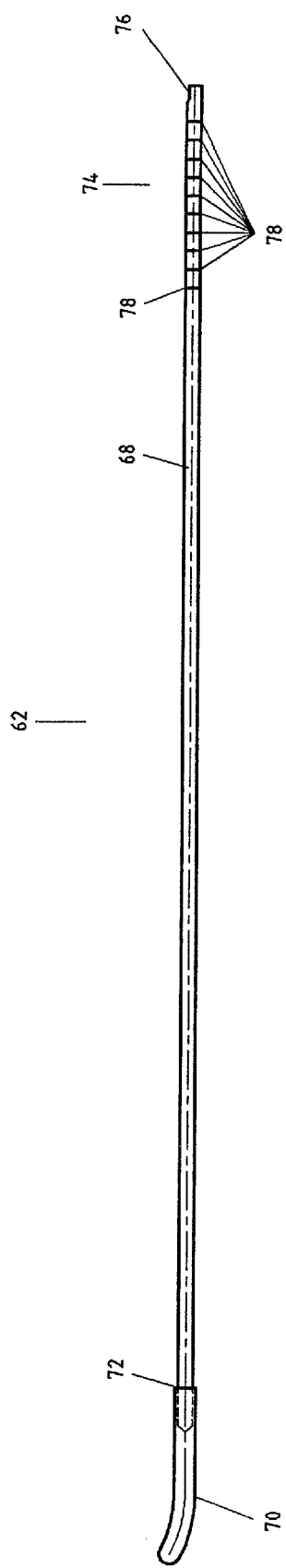
FIG. 7 is a side view of the inner manipulation shaft incorporated in the intra-uterine cannula.

Referring to FIG. 7, the manipulation shaft 62 is in the form of an elongate rod 68 having an enlarged and curved extension 70 at its proximal end 72. The extension 70 is smoothly curved and provided with a smooth surface finish in order to avoid abrasion. Further, the extension 70 has an outer diameter greater than the inner diameter of the axial bore in the cone 60 in order to ensure that it cannot slip back through the outer sheath 58. Distal end 74 of the rod 68 is provided with a flat 76 that is aligned with, and thus provides a visual indication of, the location of the upturned portion of the extension 70. The distal end 74 is also provided with a plurality of circumferential scores or markings 78 which are spaced 1 cm apart. The markings 78 are disposed along the rod 68 so that when the marking 78 closest the proximal end 72 is adjacent the distal end 16 of the sheath 58 the beginning of the extension 70 is spaced by 5 cm from the tip of the cone 60.

As previously mentioned, when the cannula 14 and in particular the outer sheath 58 is disposed within the funnel 12 the O-ring 46 in the cap 38 forms a seal between the funnel 12 and the cannula 16.

Figure 8:
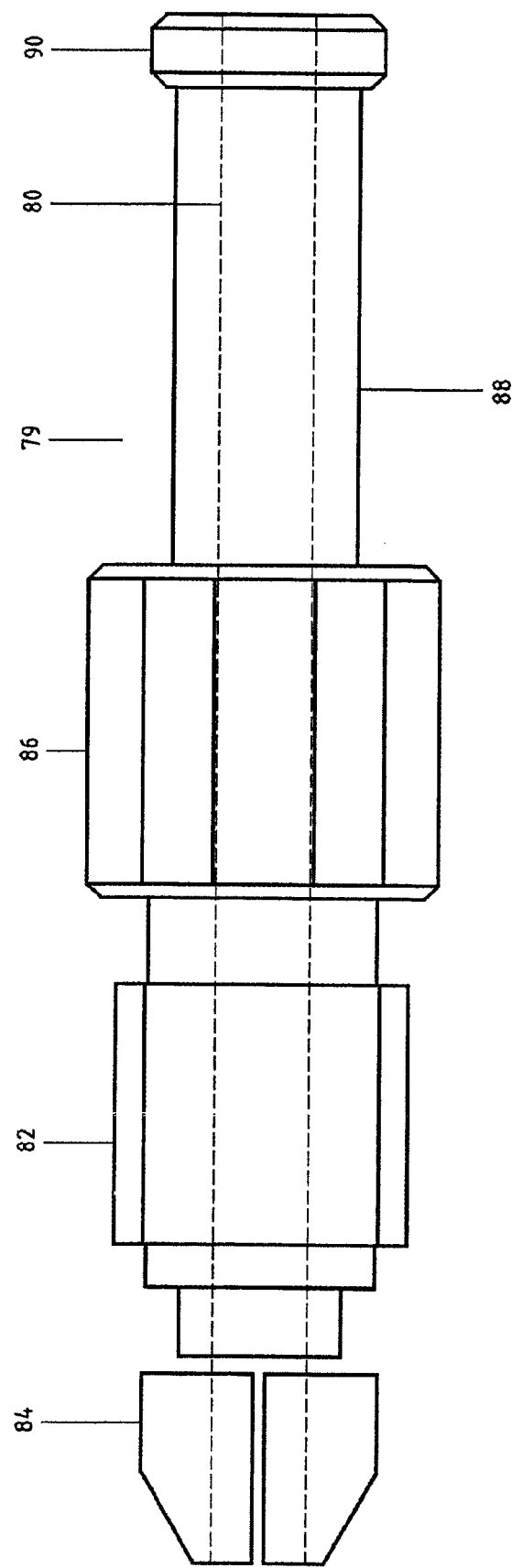
FIG. 8 is a side view of a collect incorporated in the intra-uterine cannula.

In order to hold the manipulation shaft 62 at any desired position and orientation a collet 79 is provided as shown in FIG. 8. The collet 79 has a central axial passage 80 through which the rod 68 of the manipulation shaft 62 extends. Intermediate the length of the collet 79 is a threaded cylindrical portion 82 for threadingly engaging a thread formed in the inner circumferential surface at the distal end 66 of the outer sheath 58. Forward of the portion 82 is a split head 84. In use, when the collet 78 is screwed into the outer sheath 58, the split head 84 is advanced along a portion of the inner surface of the sheath 58 that reduces in diameter. This acts to force the separate parts of the split head 84 radially together to clamp about the rod 68. On the opposite side of the thread portion 82 is an integrally formed increased diameter portion 86 and backward thereof is an integrally formed tubular length 88 provided at its end with an increased diameter flange or lip 90. As discussed in greater detail below, the tubular length 88 is gripped by a clamp of an associated instrument support to hold the cannula 14 and thus the cervical funnel 12.

Figure 9A:
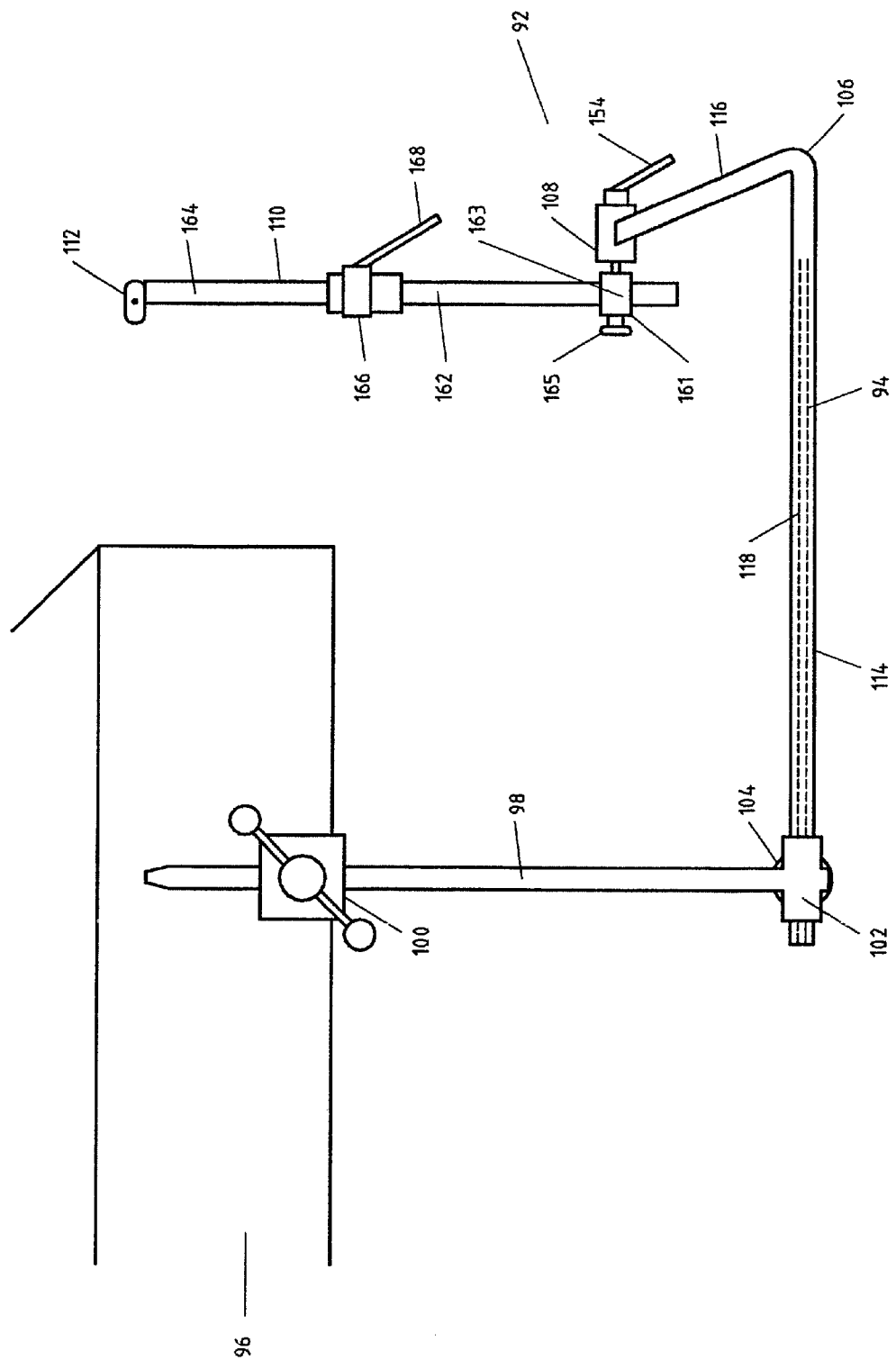
FIG. 9A is a schematic representation of a first embodiment of a support portion of the medical instrument.

FIG. 9A illustrates a support 92 (also known as a hands free uterine manipulator or HUM) incorporated in the medical instrument for supporting the cannula 14 and funnel 12. The support 92 includes an arm 94 adapted for adjustable connection or coupling to a patient's support such as a table or bed 96. In the illustrated embodiment, this coupling is by way of a drop bar 98 that is attached at its upper end by a clamp 100 to the table or bed 96 and is provided at its lower end with a perpendicularly extending hollow sleeve 102 through which the arm 94 can pass. A screw and clamp 104 is threaded to the sleeve 102 and can be rotated inwardly to clamp the arm 94 against longitudinal movement. The drop bar 98 and clamp 100 do not form part of the of the support 92. The arm 94 is formed with an elbow 106 so as to be L-shaped. Attached to the arm 94 at an end opposite that which is coupled to the drop bar 98 is a joint 108 for providing at least one (and in this instance three) degrees of motion to the cannula 14/funnel 12 when supported by the support 92. An extendible member 110 is coupled to the joint 108 to allow adjustment of the position of the funnel 12/cannula 14 in a direction of the length of the extendible member 110. An instrument holder in the form of a clamp 112 is coupled to the end of the extendible member 110. The clamp 112 clamps onto either the tubular length 88 of the collet 79 to support the cannula 14 and thus the funnel 12, or alternately toward the end of the laparoscopic hysterectomy procedure when the cannula 14 is withdrawn, the clamp 112 can be clamped about the sleeve 54 to support the funnel 12.

The arm 94 is divided into a first length 114 and a second length 116 by the elbow 106. The first length 114 is longer than the second length 116. Typically the arm 94 would be made from a length of circular cross-section metal. In order to prevent rotation of the arm 94 about the length of the first length 114, a flat 118 is machined or otherwise formed along the substantial portion of the first length 114 starting from its free end. The flat 118 is engaged by the screw clamp 104.

The joint 108 is in the form of a ball joint and is attached to the free end of second length 116. The ball joint 108 provides three degrees of rotational freedom to the extendible member 110 that in turn supports the cannula 14/cervical funnel 12. The ball joint 108 is provided with a preload so that when in an unlocked state, it can support the extendible member 110.

Referring to FIGS. 10–13 the ball joint 108 comprises a housing 120 having a central passage 122 extending axially therethrough. The passage 122 is provided with a tapered narrowing 124 at one end of the housing 120. A ball 126 to which is coupled a radially extending shaft 128 is dropped in the passage 122 so that the ball 126 rests on the narrowing 124 that prevents the ball 126 from dropping out of the housing 120. Threaded blind holes 125 are formed axially in the upper end of the housing 120.

A friction pad 130 in the form of a squat disc is dropped into the passage 122 and is provided on a surface adjacent the ball 126 with a conical recess 132 for cupping the ball 126. An opposite side of the friction pad 130 is provided with six axially extending blind holes 134. The blind holes 134 are evenly angularly spaced about the friction pad 130. The holes 134 seat one end of respective springs 136.

Figure 12A:
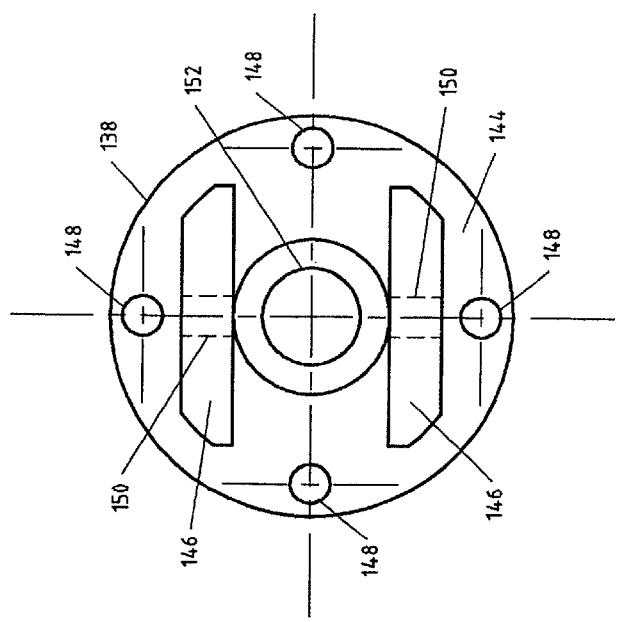
FIGS. 12a–12c are top, side and end views of a spring housing incorporated in the ball joint.
Figure 12C:
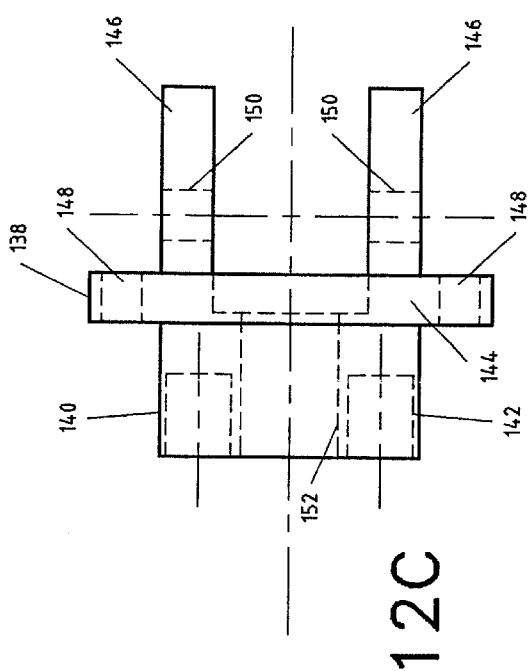
Figure 12B:
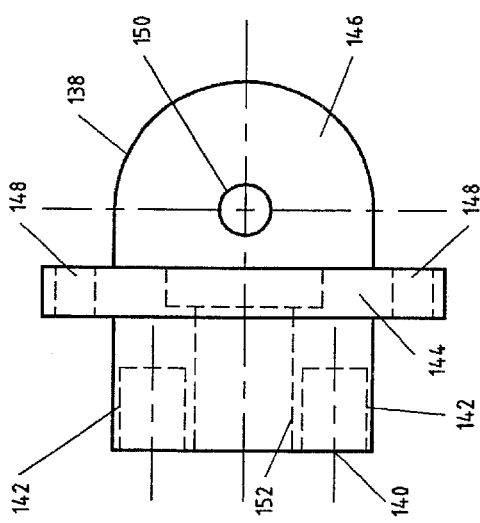

The opposite ends of the springs 136 are housed within a spring housing 138 depicted in FIGS. 12a–12c. The spring housing 138 includes a boss 140 that is dimensioned to fit inside the passage 122. The boss 140 is provided with a plurality of blind holes 142 that are juxtaposed so as to come into alignment with respective ones of the blind holes 134 so that any particular spring 136 is partially housed at one end in a blind hole 134 and at an opposite end in a blind hole 140. A coaxial and radially extending flange 144 is formed integrally across an upper end of the boss 140. On the side of the flange 144 opposite the boss 140 is a pair of spaced apart upright lugs 146.

Four axially extending through holes 148 are evenly spaced about the flange 144 near but in board of the circumferential periphery of the flange. A transversely extending through hole 150 is formed in each of the lugs 146. An axially extending hole 152 is formed through the boss 140.

The spring housing 138 is fastened to the housing 120 by means of screws passing through the holes 148 and threadingly engaging the corresponding threaded holes 125 formed in the housing 120. A nylon pin (not shown) is located in the hole 152 passing through the spring housing 138 for selectively pushing on the friction pad 130.

Figure 13:
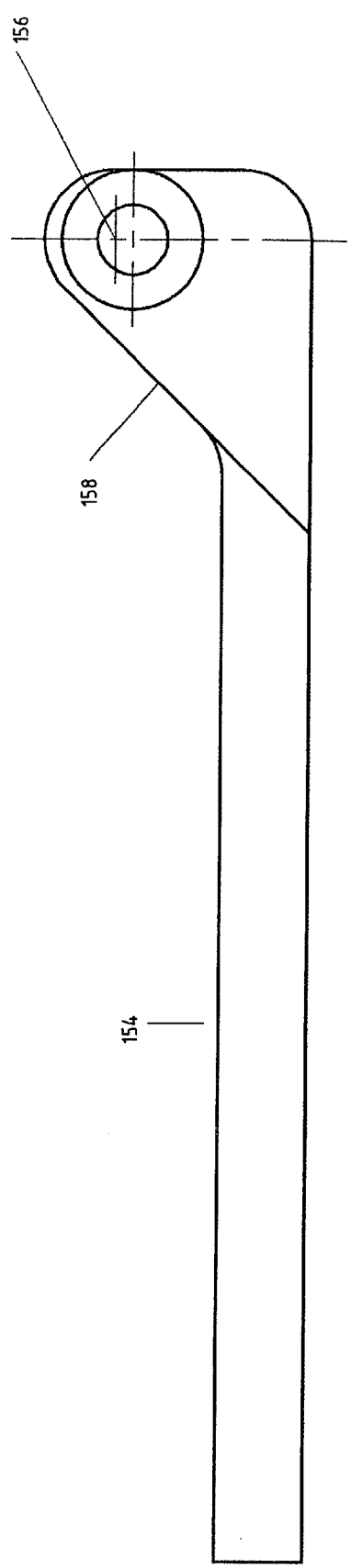
FIG. 13 is a side view of a cam lever incorporated in the ball joint.

A cam lever 154 depicted in FIG. 13 is pivotally attached between the lugs 146 by means of a pin (not shown) which passes through the holes 150 and a hole 156 formed through a cam lobe 158 at one end of the cam lever 154. The cam lobe 158 is designed so as to push against the nylon pin disposed in the hole 152 to advance that pin in the axial direction pushing it against the friction pad 130 thereby forcing the friction pad 130 into tighter contact with the ball 126 and thus locking the ball 126 in position. The spring housing 138, springs 136 and friction pad 130 are relatively dimensioned so that when fully assembled and with the cam lever 154 swung to a position where it does not contact the nylon pin the springs 136 are in compression to thereby provide a preload force on the friction pad 130 against the ball 126.

The end of length 116 of arm 94 is seated in and fastened to a recess 160 formed in the side of the housing 120.

A clamp 161 is coupled to the shaft 128 for holding the extendible member 110. The clamp 161 allows the position of the extendible member 110 to be adjusted in a direction of its length. The clamp 161 is in the form of a ring 163 through which the extendible member 110 can pass and a screw-like member 165 that can be screwed clockwise or anti-clockwise so as to be brought into abutment with or released from the extendible member 110. In this regard, a tip of the screw-like member 165 that physically contacts the extendible member 110 can also be formed with a nylon tip.

The extendible member 110 is telescopically extendible having an outer lower length 162 and an upper length 164 that can fit, slide and rotate inside the lower length 162. A cam operated clamp 166 is provided at an upper end of the upper length 162. The clamp 166 is provided with a cam lever 168 the same form as cam lever 154 which can be rotated into and out of abutment with a further nylon pin extending transversely through the clamp 166 so as to abut against the outer surface of the upper length 164. That is, the cam lever 168 can be pivoted to a position where it does not contact the nylon pin allowing the upper length 164 to slide axially and/or rotate within the lower length 162. However, as the cam lever 168 is pivoted its cam lobe comes into contact with, and progressively pushes with greater force against, the nylon pin which in turn is forced against the outer surface of the upper length 164.

An O-ring (not shown) is provided about the inside surface of the body of the clamp 166 so as to maintain contact with the outer peripheral surface of the upper length 164. This provides frictional resistance to the axial and rotation movement of the upper length 164 even when the clamp 166 is in an unclamped configuration.

Figure 14:
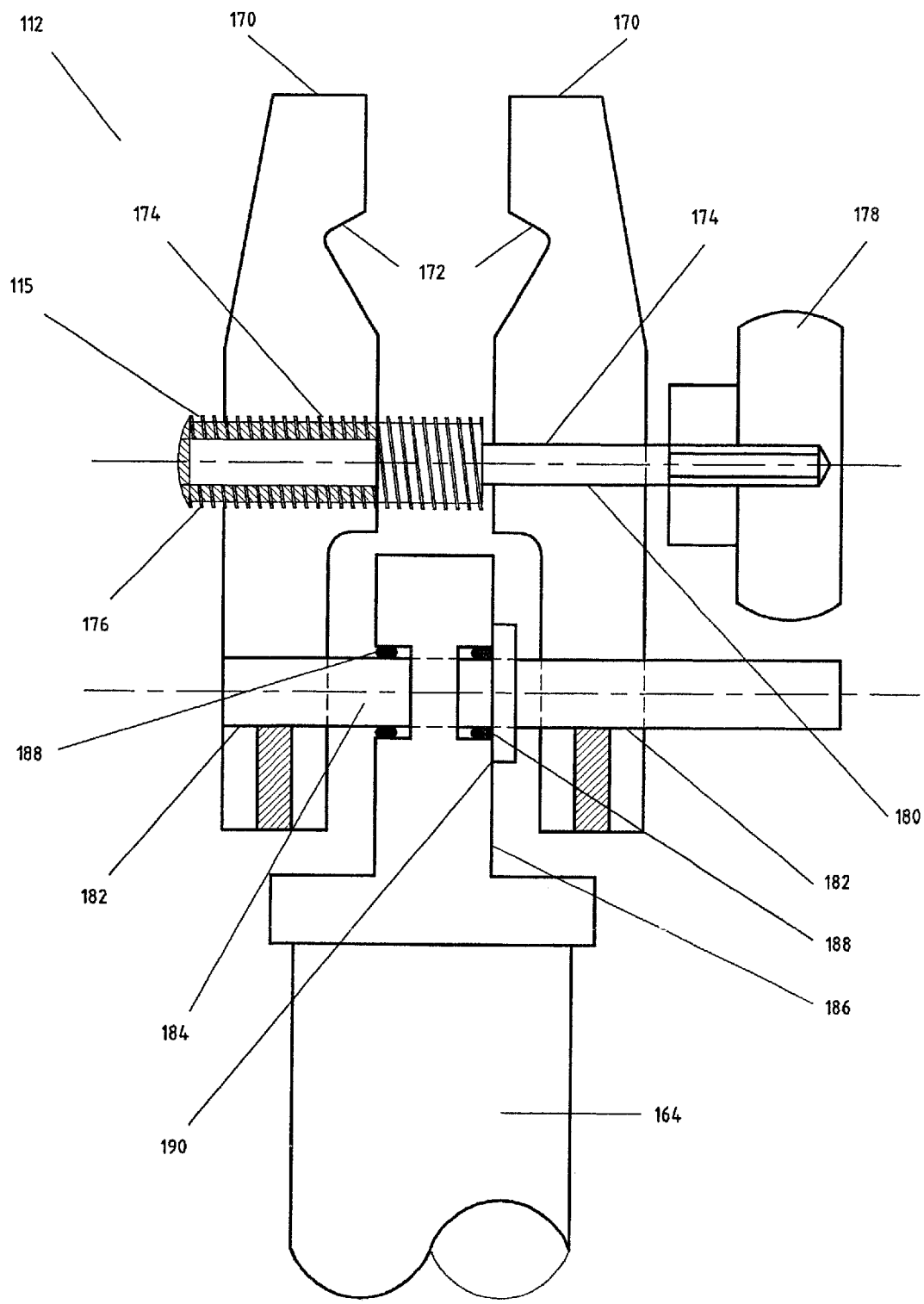
FIG. 14 is a schematic representation of a clamp incorporated in the support of FIG. 9A and 9B.

The instrument clamp 112 coupled to the end of the upper length 164 as depicted in FIG. 14. The clamp 112 comprises a pair of mutually facing clamp plates 170 which are of identical shape and configuration. The mutually facing surfaces of the plates 170 are formed with a V-shaped transversely extending recess 172. A hole 174 is formed through each plate 170 at location approximately midway along its length. An elongate screw 176 having a hand-wheel or knob 178 at one end is passed through the holes 174. At least the hole 174 on the left side plate 170, if not both holes 174 are formed with an internal thread. However the screw 176 threadingly engages only the hole 174 in the left hand side plate 170. In this regard the screw 176 is provided with a reduced diameter portion 180 that rotates freely within the hole 174 on the right hand side plate 170. The right hand plate 170 is effectively held between the larger diameter portion of the screw 176 that contains a screw thread and the knob 178.

A further hole 182 is formed in each of the plates 170 below the holes 174. A guide pin 184 is fixed inside the hole 182 on the left hand plate 170 but passes freely through the hole 182 on the right hand plate 170. The guide pin 184 also passes through an upstanding lug 186 attached to an upper end of the upper length 164. Opposite faces of the lug 186 are provided with increased diameter recesses 188 for seating respective flanges 190 formed along the guide pin 184. Rubber rings (not shown) are sandwiched between the flanges 190 and the recesses 188 to provide frictional resistance to the pivoting of the plates 170 about the pin 182.

By turning the hand-wheel 178 in a clockwise direction the plates 170 are brought closer together to enable clamping of the tubular length 88 of the cannula 12 or the sleeve 54 of the plug 48 which would be seated in the V-shaped recesses 172.

Figure 9B:
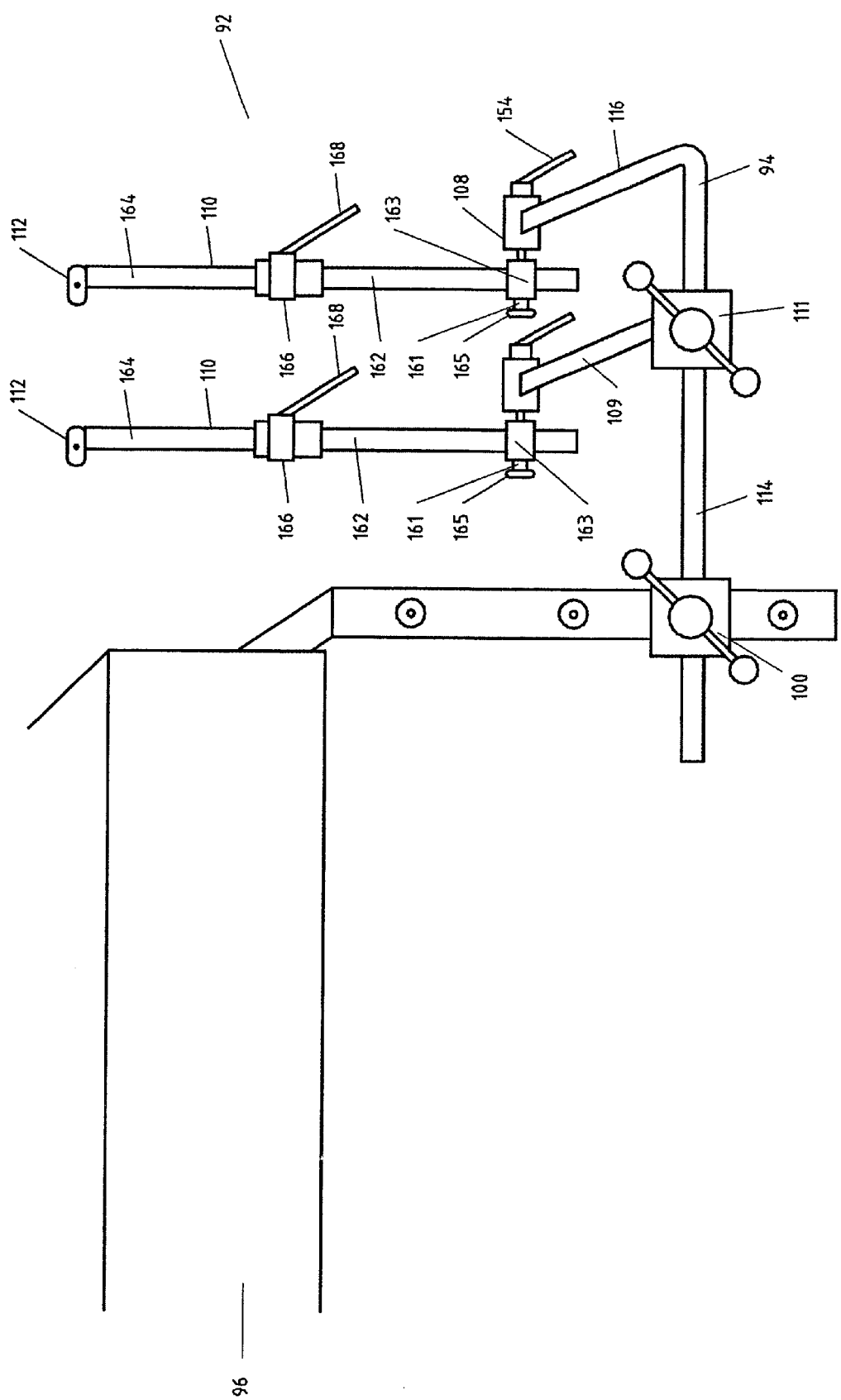
FIG. 9B is a schematic representation of a second embodiment of a support portion of the medical instrument.

FIG. 9B depicts a further embodiment of the support 92' which can be used during laparoscopic pelvic floor repair. The support 92' is very similar to, and based on, the support 92 depicted in FIG. 9A but with the addition of a second extendible member 110' for supporting a rectal probe or cannula (not shown). The member 110' is attached via joint 108' to a bar 109 which is attached via clamp 111 to the first length 114 of the arm 94. The clamp 111 can be released and tightened to allow sliding motion of the member 110' along length 114 of arm 94. A further minor difference between supports 92 and 92' is that the support 92' is attached via clamp 100' on a vertically extending plate 113 of the table or bed 96'. The plate 113 effectively replaces the drop bar 98 depicted in FIG. 9A. The remaining items of the member 110' depicted in FIG. 9B, ie joint 108', shaft 128', clamp 161', ring 163', screw-like member 165', lower and upper lengths 162' and 164' respectively, clamp 166' and cam levers 168' and 154' are of identical construction and operation to the equivalent features of the member 110 described in relation to FIGS. 9A and 10–14.

Figure 15:
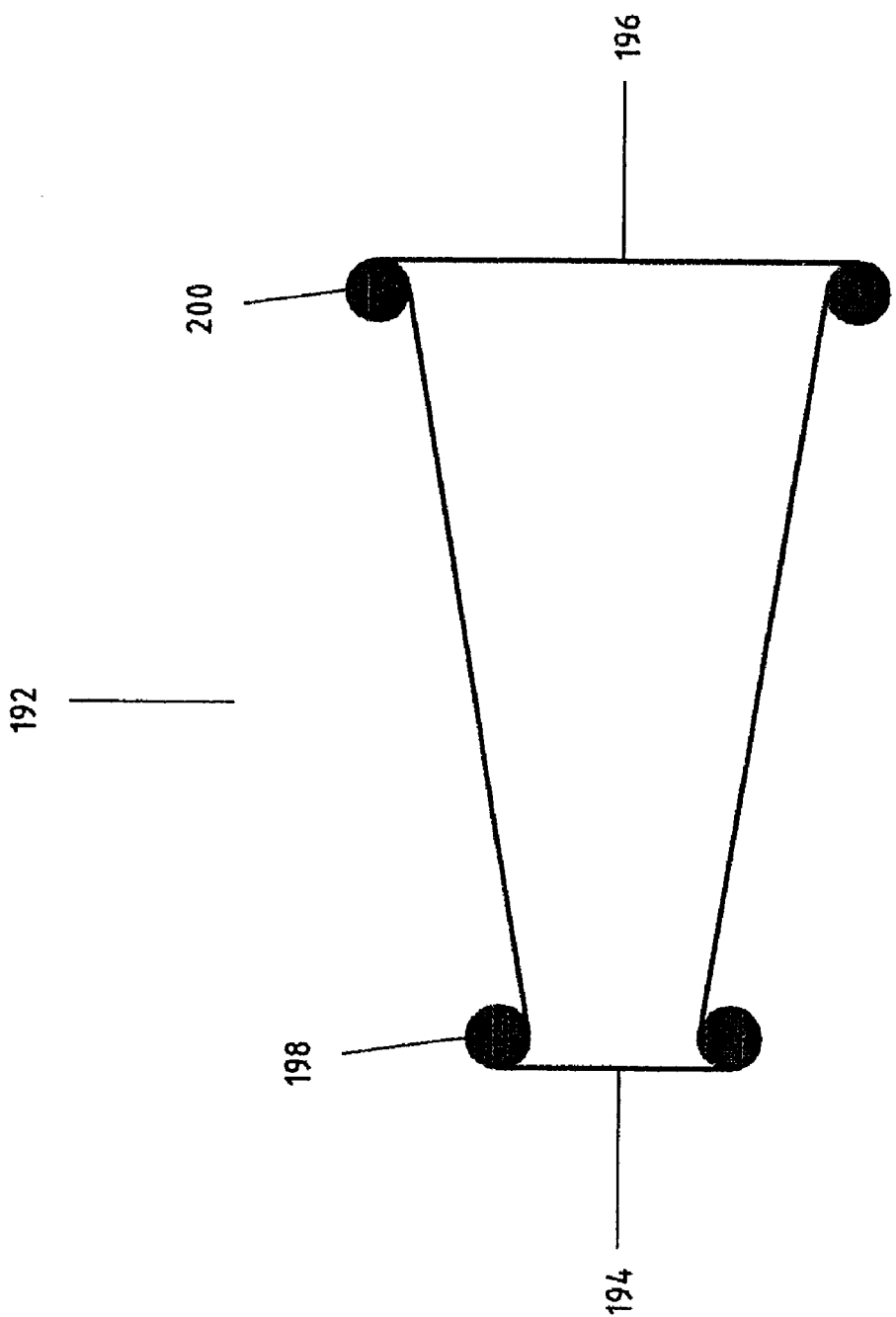
FIG. 15 is a schematic representation of a first embodiment of a seal incorporated in the medical instrument.

In order to avoid the loss of pneumoperitoneum a seal 192 of the type depicted in FIG. 15 can be incorporated into the instrument 10. The seal 192 is in the shape of a conical frustum having a small diameter end 194 and an opposite large diameter end 196. Respective resilient O-rings 198 and 200 are provided about the small and large diameter ends 194 and 196. The ring 198 is dimensioned so as to form a seal about the outer surface of the tube 16 adjacent the proximal end 18 of the funnel 12 (refer FIG. 1). The seal 192 is placed on the instrument 10 so that the large diameter end 196 is located over the cone-shaped member 20. The O-ring 200 is of a diameter greater than that of the cone-shaped member 20 and is designed to bias against the wall of the cavity in which the instrument 10 is inserted. Advantageously, the seal 192 is made from a resilient material such as a thin-walled rubber. In use, gas pressure in the cavity in which the instrument 10 is inserted acts between the seal 192 and the outer surface of the cone-shaped member 20 inflating the body of the seal 192 against the wall of the cavity and thus sealing the cavity. The bias of the O-ring 200 ensures a separation between the seal 192 and the cone-shaped member 20 within which the gas pressure can operate to inflate the seal 192. As previously mentioned, the O-ring 198 forms a seal against the tube 16 thus preventing loss of pneumoperitoneum between the seal 192 and the tube 16.

Figure 16:
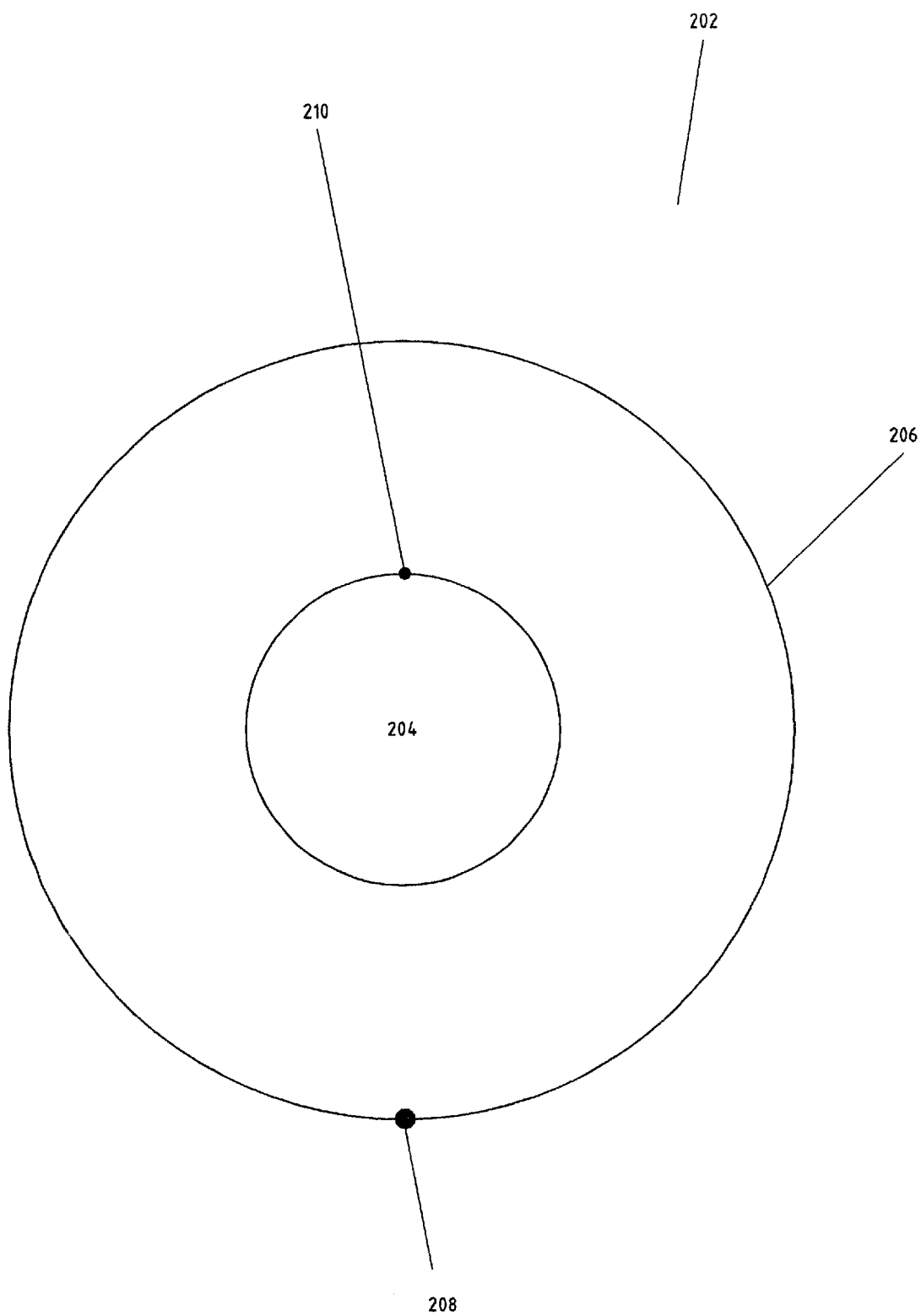
FIG. 16 is a schematic representation of a second embodiment of a seal incorporated in the medical instrument; and, FIG. 17 is a side view of a second embodiment of the intra-uterine cannula.
Figure 17:
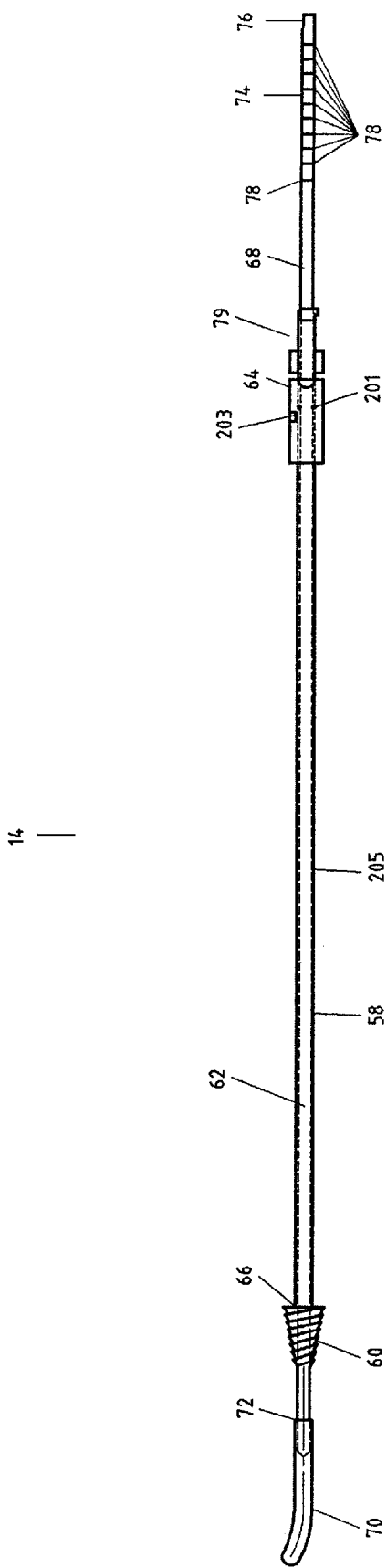

An alternate form of seal 202 is depicted in FIG. 16. The seal 202 is in the form of a donut-like ring having a central hole 204 through which tube 16 can pass. An outer circumferential surface 206 of the ring 202 contacts the vaginal wall. A valve 208 is provided to allow inflation and deflation of the ring 202. Inflation can be achieved by means of gas such as air, by a liquid such as water or saline, or by a gel. When the ring 202 is inflated its inner circumferential surface 210 forms a seal against the outer peripheral surface of tube 16 and the outer peripheral surface 206 forms a seal against the vaginal wall.

Although either seal 192 shown in FIG. 15 or seal 202 shown in FIG. 16 can be used with instrument 10 the seal 192 is preferred.

The method of operation of the instrument 10 will now be briefly described.

Initially, the SINGH cannula 14 is inserted through the vagina and the tube 16 rotated so the cone 60 threadingly engages and seals the uterus. The manipulation shaft 62 is then adjusted in its length of extension from the cone 60 to locate the fundus (the top of the uterus). This prevents the uterus from being punctured or damaged during pelvic surgery. The collet 79 can then be screwed fully into the distal end of the tube 16 to lock the manipulation shaft 62 in place. A purse-string cervical suture may be applied to hold the cone 60 in place. This further allows for the easy extraction of the uterus through the vaginal vault after delineation of the T.L.H. Next the cervical funnel 12 is slid over the cannula 14 and pushed through the vaginal tunnel into a position where the cone-shaped member 20 receives the lower end of the cervix. The combination of the cannula 14 and funnel 12 is then supported by the support 92 by clamping the tubular length 88 of the collet 79 between the plates 170 of clamp 112. Thus, no assistant is required to hold or manipulate the cannula 14 or the funnel 12. The surgeon can effect rotation or axial motion of the funnel 12 by simply gripping the cap 38 and applying the appropriate force by hand. However if a rotational-type, sideways or up and down motion is required the surgeon is able to manipulate the support 92 by way of ball joint 108, clamp 166, clamp 122 or screw clamp 104 of the support 92 to make the appropriate adjustment. Prior to dissection of the uterus, the seal 192 is slid onto tube 16 with O-ring 198 forming a seal on the tube 16 and O-ring 200 located over the cone-shaped member 20.

When the laparoscopic hysterectomy is complete, the combination of the funnel 12 and cannula 14 are withdrawn. Thereafter, the funnel 12 fitted with the plug 48 and the seal 192 is reintroduced to maintain pneumopertoneum while the vaginal vault is sutured.

Consequential to the invention a variation of the SINGH cannula 14 has been developed for diagnostic purposes. This SINGH cannula 14' is depicted in FIG. 16. The SINGH cannula 14' is quite similar to the cannula 14 and includes an outer sheath 58 provided with a cone 60 at its proximal end 66 and an internal manipulation shaft 62 having an elongate rod 68 which is attached the curved extension 70 at its proximal end 72. The distal end 74 is provided with a flat 76 and a plurality of circumferential markings 78. The cannula 14' differs from the cannula 14 by the inclusion of an O-ring 201 near distal end 64 of the sheath 58. The O-ring 201 forms a gas seal between the inner circumferential surface of sheath 58 and the outer surface of the rod 68.

A further difference is that in the cannula 14' has an increased diameter portion near distal end 66 through which an inlet port 203 is formed to provide fluid communication to an annular space 205 formed between the rod 68 and the inner surface of the sheath 58. The O-ring 201 is behind the port 204 and forms a seal so that fluid introduced through the port 203 cannot pass from the distal end 64 of the shaft 58. This allows fluid to be pumped or channelled through the inlet port 203 and the passage 205 to pass out from the tip of the cone 60 into the uterus allowing hydrotubation. In all other respects the cannula 14 prime can be manipulated in the same manner as the cannula 14 described above.

All modifications and variations of the invention that would be apparent to a person of ordinary skill in the art are deemed to be within the scope of the present invention the nature of which is to be determined from the above description.

That which is claimed is:

1. A medical instrument 10 for gynecological surgery comprising:
    a cervical funnel 12 having an elongated hollow tube 16 with a proximal end 18 for insertion into a vagina of a patient and a hollow substantially cone-shaped member 20 provided at the proximal end of the hollow tube, the cone-shaped member having an outer diameter that reduces in a direction extending toward a distal end 22 of the hollow tube and having a mouth 24 with an inner diameter greater than a diameter of the opening of the patient's cervix; and
    an intra-uterine cannula 14 having an outer sheath 58 axially and rotatably moveable within said hollow tube 16, the outer sheath having a proximal end 64 and an opposite distal end 66, respectively locatable outside the proximal 18 and distal ends 22 of the hollow tube; sealing means 60 provided at the proximal end 64 of the sheath for engaging the cervix to seal the uterus of the patient; and an inner manipulation shaft 62 axially and rotatably moveable within the outer sheath and extending axially through the sealing means 60.

2. The instrument recited in claim 1, wherein the cone-shaped member mouth has a protruding lip extending outwardly along a portion of a circumference of the mouth, the lip for providing a cutting surface for lifting a section of vaginal vault away from an adjacent internal organ.

3. The instrument recited in claim 2, wherein the lip extends about the mouth circumference through an arc that subtends an angle of approximately 120°.

4. The instrument recited in claim 3, wherein the lip protrudes at an angle of approximately 45° to a longitudinal axis of the cone-shaped member.

5. The instrument recited in claim 4, wherein the lip protrudes from the mouth circumference approximately 5–10 mm.

6. The instrument recited in claim 4, wherein the hollow tube has a mark at the distal end corresponding generally to an angular position of a circumferential midpoint of the lip, for facilitating a visualization of a position of the lip during a surgical procedure.

7. The instrument recited in claim 6, wherein the cone-shaped member comprises a plastic material.

8. The instrument recited in claim 1, wherein the cone-shaped member is removably attached to the hollow tube proximal end, for facilitating replacement.

9. The instrument recited in claim 1, wherein the sealing means comprises a cone having a thread formed along an outer surface thereof, the cone tapering outwardly toward an end adjacent the outer sheath proximal end.

10. The instrument recited in claim 1, further comprising releasable locking means operable to releasably lock the inner manipulation shaft to the outer shaft.

11. The instrument recited in claim 1, wherein the outer sheath has an inlet port for permitting hydrotubation to be performed therethrough.

12. The instrument recited in claim 1, wherein the manipulation shaft comprises a plurality of markings adjacent the distal end for providing an indication of uterus length.

13. The instrument recited in claim 1, further comprising a fluid seal positioned in surrounding relation to an outer surface of the cervical funnel, the fluid seal having a frustro-conical shape, a small-diameter end in sealing relation to an outer surface of the hollow tube, and a large-diameter end positioned over the cone-shaped member, the large-diameter end having a diameter greater than a diameter of the cone-shaped member.

14. The instrument recited in claim 13, further comprising a resilient ring positioned about the large-diameter end of the fluid seal.

15. A gynecological surgical system comprising:
    a cervical funnel having an elongated hollow tube with a proximal end for insertion into a vagina of a patient and a hollow substantially cone-shaped member provided at the proximal end of the hollow tube, the cone-shaped member having an outer diameter that reduces in a direction extending toward a distal end of the hollow tube and having a mouth with an inner diameter greater than a diameter of the opening of the patient's cervix;

an intra-uterine cannula having an outer sheath axially and rotatably moveable within said hollow tube, the outer sheath having a proximal end and an opposite distal end, respectively locatable outside the proximal and distal ends of the hollow tube; sealing means provided at the proximal end of the sheath for engaging the cervix to seal the uterus of the patient; and an inner manipulation shaft axially and rotatably moveable within the outer sheath and extending axially through the sealing means; and means for supporting the cannula and funnel comprising:
an arm couplable to a patient support;
a first adjustable joint attached to the arm for providing a degree of motion;
a first extendible member coupled to the first joint;
an instrument holder attached to an end of the first extendible member having means for holding the cannula.

16. The system recited in claim 15, wherein the joint is adapted to provide three degrees of rotational motion, permitting pitch, roll, and yaw position control of the extendible member and thus the cannula.

17. The system recited in claim 16, wherein the joint comprises a ball joint having releasable locking means movable between a locked state for locking a position of the extendible member and an unlocked state for permitting an adjustment of a position of the extendible member.

18. The system recited in claim 17, wherein the extendible member comprises a telescopically movable member.

19. The system recited in claim 18, wherein the supporting means further comprises a clamp means for releasably coupling the extendable member to the joint for permitting an adjustment of a position of the extendible member in a direction along a length thereof.

20. The system recited in claim 15, wherein the supporting means further comprises a second extendible member coupled to the arm, the second extendible member adapted to hold a rectal probe.

21. The system recited in claim 20, wherein the supporting means further comprises:
a bar;
a releasable clamp adapted to couple an end of the bar to the arm; and
a second adjustable joint adapted to attach the second extendible member to an opposite end of the bar.

22. A method for performing a gynecological procedure comprising the steps of:
providing an instrument comprising:
a cervical funnel having an elongated hollow tube with a proximal end for insertion into a vagina of a patient and a hollow substantially cone-shaped member provided at the proximal end of the hollow tube, the cone-shaped member having an outer diameter that reduces in a direction extending toward a distal end of the hollow tube and having a mouth with an inner diameter greater than a diameter of the opening of the patient's cervix; and
an intra-uterine cannula having an outer sheath axially and rotatably moveable within said hollow tube, the outer sheath having a proximal end and an opposite distal end, respectively locatable outside the proximal and distal ends of the hollow tube; sealing means provided at the proximal end of the sheath for engaging the cervix to seal the uterus of the patient; and an inner manipulation shaft axially and rotatably moveable within the outer sheath and extending axially through the sealing means;
inserting the cannula into a vagina of the patient;
rotating the tube until the cone-shaped member engages and seals a cervix of the patient;
adjusting a length of the manipulation shaft so that a distal end thereof opposes a fundus of the patient;
sliding the cervical funnel over the cannula, through the vagina to a position wherein the cone-shaped member receives a lower end of the cervix; and
supporting the cannula and funnel for permitting a subsequent manipulation.

* * * * *